(12) United States Patent
Pellegretti et al.

(10) Patent No.: US 11,402,354 B2
(45) Date of Patent: Aug. 2, 2022

(54) METHOD FOR GENERATING ULTRASOUND TRANSMISSION WAVES AND ULTRASOUND SYSTEM FOR CARRYING OUT THE SAID METHOD

(71) Applicant: ESAOTE SpA, Genoa (IT)

(72) Inventors: Paolo Pellegretti, Genoa (IT); Marco Crocco, Ovada (IT); Fulvio Biordi, Genoa (IT)

(73) Assignee: Esaote S.p.A., Genoa (IT)

( * ) Notice: Subject to any disclaimer, the term of this patent is extended or adjusted under 35 U.S.C. 154(b) by 243 days.

(21) Appl. No.: 16/894,737

(22) Filed: Jun. 5, 2020

(65) Prior Publication Data

US 2020/0393420 A1    Dec. 17, 2020

(30) Foreign Application Priority Data

Jun. 12, 2019  (EP) .................................. 19179597

(51) Int. Cl.
*G01N 29/34*    (2006.01)
*A61B 8/00*    (2006.01)
(Continued)

(52) U.S. Cl.
CPC ......... *G01N 29/348* (2013.01); *A61B 8/4488* (2013.01); *G01N 29/24* (2013.01);
(Continued)

(58) Field of Classification Search
CPC .... G01N 29/348; G01N 29/24; G01N 29/346; A61B 8/4488; G01S 15/8915;
(Continued)

(56) References Cited

U.S. PATENT DOCUMENTS 5,523,058 A  *  6/1996  Umemura ................ A61N 7/02
                                            366/127
5,913,823 A     6/1999  Hedberg
                      (Continued)

FOREIGN PATENT DOCUMENTS

EP           2063289 A2    5/2009

OTHER PUBLICATIONS

European Search Report dated Dec. 9, 2019, which issued in corresponding EP Patent Application No. EP19179597.0.

*Primary Examiner* — Helen C Kwok
(74) *Attorney, Agent, or Firm* — Dickinson Wright PLLC

(57) ABSTRACT

A method is provided for generating ultrasound transmission waves comprising: a) providing an array of electroacoustic transducer elements each one being connected to an electric excitation signal generator by a dedicated feeding channel; b) feeding at least a part of the electroacoustic transducer elements with a pulsed electric signal having a predetermined frequency, a predetermined amplitude, a predetermined length or duration and a predetermined phase or a predefined delay with respect to the pulsed electric signals fed to the adjacent transducer elements, the said pulsed electric excitation signals comprising a sequence of pulses; c) modulating each or at least part of the pulsed electric signals by feeding to the transducer elements only a predetermined portion of the pulses of the said pulsed electric signals. Modulating is carried out by cutting the duration of each pulse of the pulsed electric excitation signal according to a predetermined time period.

16 Claims, 8 Drawing Sheets

(51) Int. Cl.
 *G01N 29/24* (2006.01)
 *G01S 7/524* (2006.01)
 *G01S 15/89* (2006.01)

(52) U.S. Cl.
 CPC ............ *G01N 29/346* (2013.01); *G01S 7/524* (2013.01); *G01S 15/8915* (2013.01); *G01N 2291/106* (2013.01)

(58) Field of Classification Search
 CPC .... G01S 7/524; G01S 7/5202; G01S 7/52047; B06B 1/0215; G01K 11/346
 See application file for complete search history.

(56) References Cited

U.S. PATENT DOCUMENTS

| | | | |
|---|---|---|---|
| 6,135,963 A | 10/2000 | Haider | |
| 6,193,659 B1 | 2/2001 | Ramamurthy | |
| 2015/0063073 A1* | 3/2015 | Takahata | G01S 7/524 367/137 |
| 2015/0348531 A1* | 12/2015 | Freear | B06B 1/0215 367/137 |
| 2017/0090507 A1* | 3/2017 | Wiener | H03K 5/01 |

\* cited by examiner

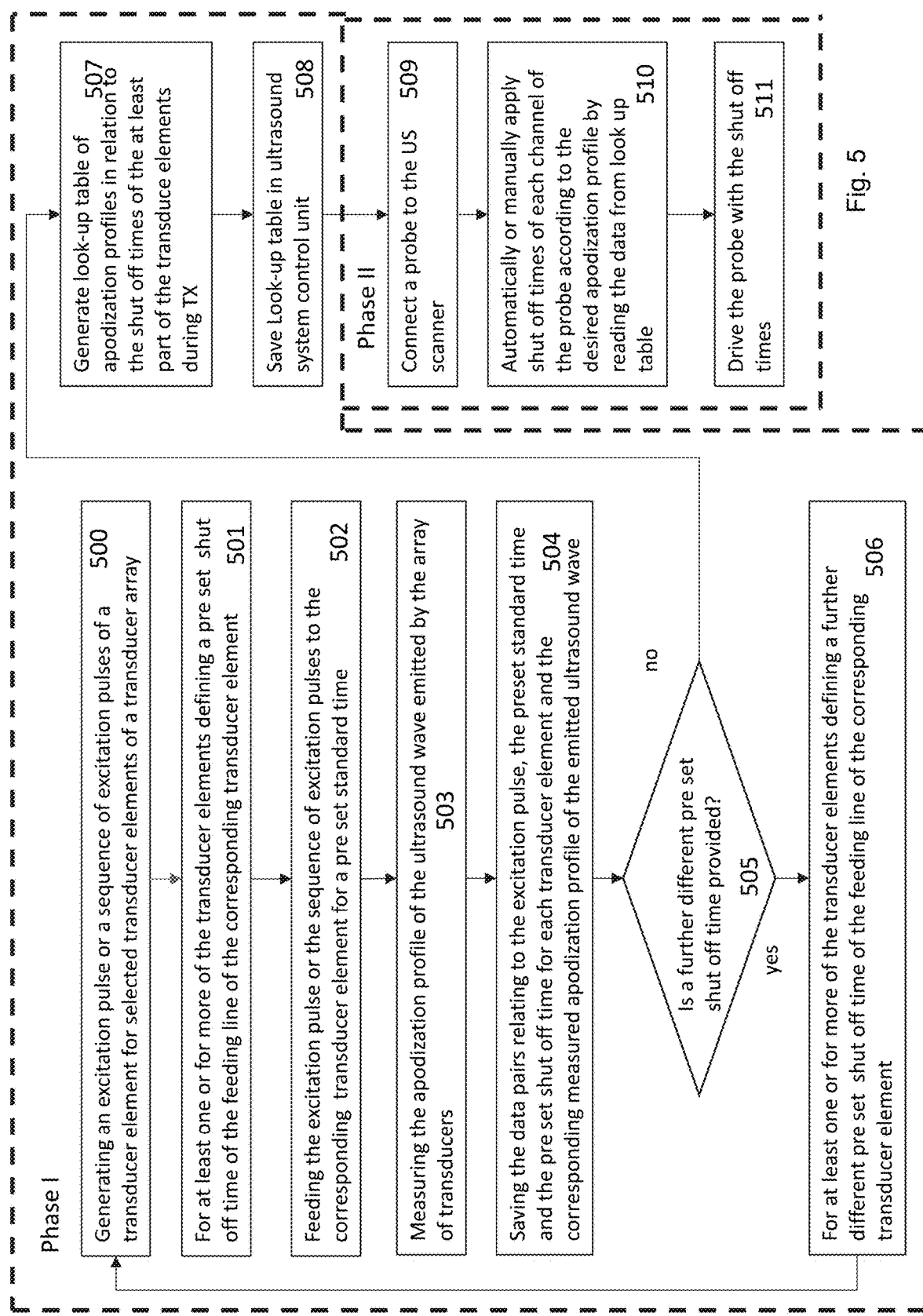

METHOD FOR GENERATING ULTRASOUND TRANSMISSION WAVES AND ULTRASOUND SYSTEM FOR CARRYING OUT THE SAID METHOD

BACKGROUND OF THE INVENTION

The present disclosure relates to a method for generating ultrasound transmission waves comprising:
a) providing an array of electroacoustic transducer each one being connected to an electric excitation signal generator by a dedicated feeding channel;
b) feeding at least a part of the electroacoustic transducers with a pulsed electric signal having a predetermined frequency, a predetermined amplitude, a predetermined length or duration and a predetermined phase or a predefined delay with respect to the pulsed electric signals fed to the adjacent transducer elements, the said pulsed electric excitation signals comprising a sequence of pulses;
c) modulating each or at least part of the pulsed electric signals by feeding to the transducer elements only a predetermined portion of the pulses of the said pulsed electric signals.

Ultrasound imaging is a commonly used technique to non-invasively acquire images of the internal anatomy or physiology of the body of a patient. Ultrasound images are obtained by transmitting ultrasound wave pulses into a region of a body and receive the reflected ultrasound waves. Transmit ultrasound waves are generated by exciting separately and independently one from the other a certain number of electroacoustic transducer elements which following the excitation emits an acoustic wave. The frequency of the excitation signal is related to the frequency of the emitted acoustic signal. In Ultrasound imaging the frequency of the emitted acoustic signals is in the field of the ultrasound. The electroacoustic transducers are grouped forming an array of transducers in which the elements are positioned according to a predefined distribution pattern or topology. Each transducer element generates when excited an acoustic signal which contributes as a component to the ultrasound wave emitted by the transducer array. In order to generate an acoustic wave having a certain profile or wave form the waves emitted by the single transducer elements are shifted in phase or delayed so to combine in a constructive or destructive manner. In this way an ultrasound wave is formed which can have a wave front of a certain profile and which can be focalized at a certain depth.

Ultrasound signals reflected by the target body in which the emitted ultrasound waves has been transmitted are received by a group of electroacoustic transducers, usually the same ones used for the transmission. The ultrasound signals are transformed in electric signals by each transducer element. Realigning the signal component of each transducer element in relation to the time of arrival of the said component from a certain reflection point in the target body allows to reconstruct the acoustic signal reflected from this reflection point by constructively summing the signal components received by the transducer elements of the group of transducers.

The quality of images that can be produced by these waves is the point spread function of the transmit beam used to apply ultrasound signals to the patient's body. In fact, the acoustic power of an ultrasound wave even when the ultrasound wave or beam is generated by focusing the beam through the above-mentioned delay and sum process, is distributed on a main and on side lobes of the energy pattern distribution of the acoustic signal. Sidelobes have the effect of lowering the quality of the images limiting contrast resolution and dynamic.

To achieve the highest contrast resolution and good dynamic as well as best IQ performances the ultrasound beam that is transmitted into the patient should have as low sidelobes as possible.

One method of improving the quality of ultrasound images is to transmit signals from an ultrasound transducer with an apodization function that reduces the acoustic power of the signals transmitted from the sides of the transducer while allowing an increased acoustic power to be transmitted from those transducer elements near the center of the transducer. This has the effect of reducing the sidelobes in the transmit beam.

According to the state of the art, it is known to apply apodization of the ultrasound wave generated by the transducer array of an ultrasound probe by modifying the amplitude of the ultrasound contribution emitted by the peripheral or lateral transducer elements of the array of transducer elements relatively to the amplitude of the other transducer elements which are at the center or in the neighborhood of the center of the transducer array according to a predefined function of the reduction of the amplitude in relation to the position of the transducer element in the array of transducer elements. One way of carrying out this method of applying apodization comprises using a separate voltage regulator in line with each individual piezoelectric crystal, i.e. with each transducer element in the array of transducer elements. This approach is costly.

In the state of the art a different approach is known for applying apodization to an acoustic beam such as an ultrasound beam or wave generated by an array of transducers. This approach uses a pulser for generating a pulsed electric excitation signal comprising a sequence of pulses and applies Pulse-Width-Modulation (PWM) to tune pulse-energy per each acoustic TX pulsers contributing to the overall beam generation. Also this approach, although effective, has some drawbacks. It needs many hardware resources to manage the Pulse Width Modulation. Furthermore, it needs a lot of configuration data to upload to the transmit front end such as different waveforms for each transmission channel and consequently each transmission transducer element.

SUMMARY

A first object is to provide a method which can be effectively implemented by using presently cost-effective transmission architectures such as dedicated/integrated bipolar/multilevel pulsers.

A further object is to achieve an effective reduction of the side lobes of the ultrasound transmission beams or waves getting top IQ performances as high contrast resolution and dynamic.

Still a further object is to simplify the process of driving the transducer elements of a transducer array by using limited and simple hardware resources and a negligible increase of data for configuration of the hardware governing the transmit channels.

According to a first embodiment there is a method for generating ultrasound transmission waves comprising:
a) providing an array of electroacoustic transducer elements each one being connected to an electric excitation signal generator by a dedicated feeding channel;
b) feeding at least a part of the electroacoustic transducer elements with a pulsed electric signal having a predetermined frequency, a predetermined amplitude, a predetermined length or duration and a predetermined phase or a predefined delay with respect to the pulsed electric signals fed to the adjacent transducer elements, the said pulsed electric excitation signals comprising a sequence of pulses;

c) modulating each or at least part of the pulsed electric signals by feeding to the transducer elements only a predetermined portion of the said pulsed electric signals, wherein c) is carried out by cutting the duration of the said pulsed electric excitation signal according to at least one or more than one predetermined time periods.

According to a first embodiment, the pulsed signal is cut off by putting it to zero amplitude for a time interval corresponding to one time interval or for a series of time intervals each one of the said time interval of the said series corresponding to a fraction of a pulse of the sequence of pulses forming the pulsed signal.

According to an embodiment, the pulsed electric excitation signals driving each of the said at least part of transducer elements of the transducer array are formed by a sequence of pulses having a predetermined cycle and duration and the signals has a predetermined total duration, while the duration of the time period in which the pulse is cut off is applied to each pulse of the sequence of pulses.

According to still a further embodiment which can be provided in combination with the above embodiments, the duration of the cut off of each pulse is different for at least part of the said transducer elements and is set such that transducer elements at the outer edges of the transducer array transmit a lesser percentage of a pulse than those transducer elements located at the center of the transducer.

According to an embodiment herein the cut off of the pulses of the excitation signals is carried out by shutting off or interrupting the feeding channel of the corresponding transducer element.

According to still another embodiment, the following operations are provided:

d) providing a probe having a transducer array;
e) Carrying out operations a) to c) for a set of different periods of cut off for each one of the said at least part of electroacoustic transducers and for each combination of cut off periods applied to the said at least part of acoustic transducers simulating by calculation the profile of the ultrasound wave theoretically generated by the array of transducers driven with the said cut off periods or measuring the profile of the ultrasound wave generated by the array of transducers and saving the said combination of cut off periods and the corresponding profile of the simulated or of the measured acoustic wave;
f) Generating a look up table describing the relation between profile of the generated acoustic wave and a set of cut off periods for the said at least part of electric transducers.

According to further embodiments, once a look up table has been generated according to the above combination of steps, the said look up table is used for reading the values of the cut off periods from the look up table corresponding to a desired acoustic wave profile, i.e. apodization profile of the wave front of the transmitted ultrasound wave and the said cut off periods are applied to the pulsed excitation signals of the corresponding transducer elements for generating an acoustic wave.

According to an embodiment, a method for generating ultrasound waves comprises the steps of:

Providing a probe, the probe comprising an array of electroacoustic transducer elements;

Selecting a look up table of the cut off periods corresponding to the said probe, the look up table being generated according to the combination of steps disclosed above;

generating pulsed electric excitation signals for at least part of the transducer elements;

modulating the excitation signals of the at least part of the transducer elements according to the cut off period taken from the look up table;

feeding the modulated excitation signals to the corresponding electroacoustic transducer elements.

Thanks to the above method, the ultrasound transmission wave can be generated by using the same transmit waveform shared by all transmit channels. This means that each transducer element is fed by a pulsed electric excitation signal having the same waveform.

Simply providing signal shut off periods for modulating the energy transmitted by the single transducer elements can be obtained by interrupting the corresponding channel feeding the excitation signal to the corresponding transducer element. This can be obtained by using a dedicated switch in each feeding line of each transducer element. The switch can be controlled by a controller and commutated alternatively for periods of preestablished length in a closed or in an open state, thus alternatively allowing the passage to the transducer element of the excitation signal or preventing the said passage.

In order to configurate the system it is merely necessary to choose the desired profile of the transmitted ultrasound wave and to read from the look up table the channel shut off periods to be applied to the feeding lines of each one or of at least some of selected transducer elements.

The said look up table can be generated by experiment or by simulation by means of functions describing the physics of the process only once for a selected kind of probe or for a selected kind of transducer array. This process can be carried out only once for each probe or transducer array in an inhouse process and the lookup tables obtained can be used by loading in the control system of each ultrasound system which can be used in combination with the said probe.

According to a further feature, when a certain probe is provided in an ultrasound system, upon choice of the profile of the generated ultrasound wave, the system can automatically select the look-up table corresponding to the probe and set the corresponding shut off periods of the feeding lines corresponding to each or of part of the transducer elements. These data of the shut off periods is then used to control the switches provided in the feeding lines of the said transducer elements.

When a control unit of the switches is provided the said data corresponding to the said shut off periods is loaded in the settings of the said control unit and the said control unit operates the switches according to the corresponding shut off periods.

The present invention relates also to an ultrasound system comprising:

an ultrasound probe comprising an array of electroacoustic transducer elements;

an ultrasound transmit wave generating section generating electric excitation signals of the transducer elements of the said array;

said ultrasound transmit wave generation section comprising an ultrasound waveform generator which is connected by a separate feeding line with each one of the said transducer elements or which can be connected with each one of the said transducer elements alternatively from the other transducer elements;

a pulser unit for each of the said transducer elements which is provided in the separate feeding line connected to a corresponding transducer element or which is provided in the feeding line which is alternatively connectable to each one of the said transducer elements;

A control unit controlling the said pulser unit, which control unit comprises means for modulating the pulsed signal generated by the pulser unit in such a way that only a predetermined portion of the said pulsed electric signal or of the pulses forming the said pulsed electric signal is fed to the corresponding transducer element.

According to the present invention, the control unit is configured to cutting the duration of the pulsed electric signal or of each pulse of the pulsed electric excitation signal according to a predetermined time period of shut off of each pulse or of the pulsed electric signal.

According to an embodiment, the said control unit directly operates on the pulser unit by activating and deactivating the said pulser unit according to the preestablished cut off periods of of the pulsed electric signal or of the pulses of a corresponding transducer element.

According to a variant embodiment each feeding line is provided with a switch which can be controlled by the control unit, the said control unit commutating the switch to alternatively open or close the corresponding feeding line of a transducer elements for predefined periods of conduction and of interruption of the said feeding line.

According to a further embodiment, the ultrasound system further comprises:

a memory for saving a database or a look up table comprising a plurality of profiles of the wave front of the transmitted ultrasound wave and the corresponding shut off periods to be applied to the feeding lines of each of the transducer elements of the array;

the said database or the said memory being readable by the control unit;

a wave front or apodization profile selector interface for selecting a wave front or apodization profile from the said plurality of profiles and setting the said selected profile in the control unit;

the said control unit being configured to automatically load the setting of the shut off periods related to the said wave front or apodization profile for the different feeding lines of the corresponding transducer elements and to apply this shut off periods in controlling the open and closed condition of the said switches.

According to a further embodiment, the ultrasound system comprises a probe selector for setting the type of ultrasound probe connected to the system among different types of probes compatible with the said system, the said selector automatically addressing and setting the
   database or the look up table for the selected typo of probe.

In a variant, the probe selector is an automatic selector automatically receiving or reading information of the type of the connected probe and automatically addressing and setting the database or the look up table for the selected typo of probe.

All of the above embodiment can be provided in combination with an ultrasound system comprising an ultrasound receive beam receiving section generating electric signals corresponding to the received ultrasound beams generated by reflection of the said ultrasound transmit waves or beams by reflector provided in a target body and a processor, processing the said signal for reconstructing an image and an output section for printing, saving, exporting or displaying the said image or the said image file.

BRIEF DESCRIPTION OF THE DRAWINGS

Further improvements and characteristics of the embodiments herein will be clear from the following description of some non-limiting embodiments schematically shown in the annexed figures wherein:

FIG. 5 is a flow diagram of an embodiment of the method according to the present invention.

DETAILED DESCRIPTION

While multiple embodiments are described, still other embodiments of the described subject matter will become apparent to those skilled in the art from the following detailed description and drawings, which show and describe illustrative embodiments of disclosed inventive subject matter. As will be realized, the inventive subject matter is capable of modifications in various aspects, all without departing from the spirit and scope of the described subject matter. Accordingly, the drawings and detailed description are to be regarded as illustrative in nature and not restrictive.

Figure 1:
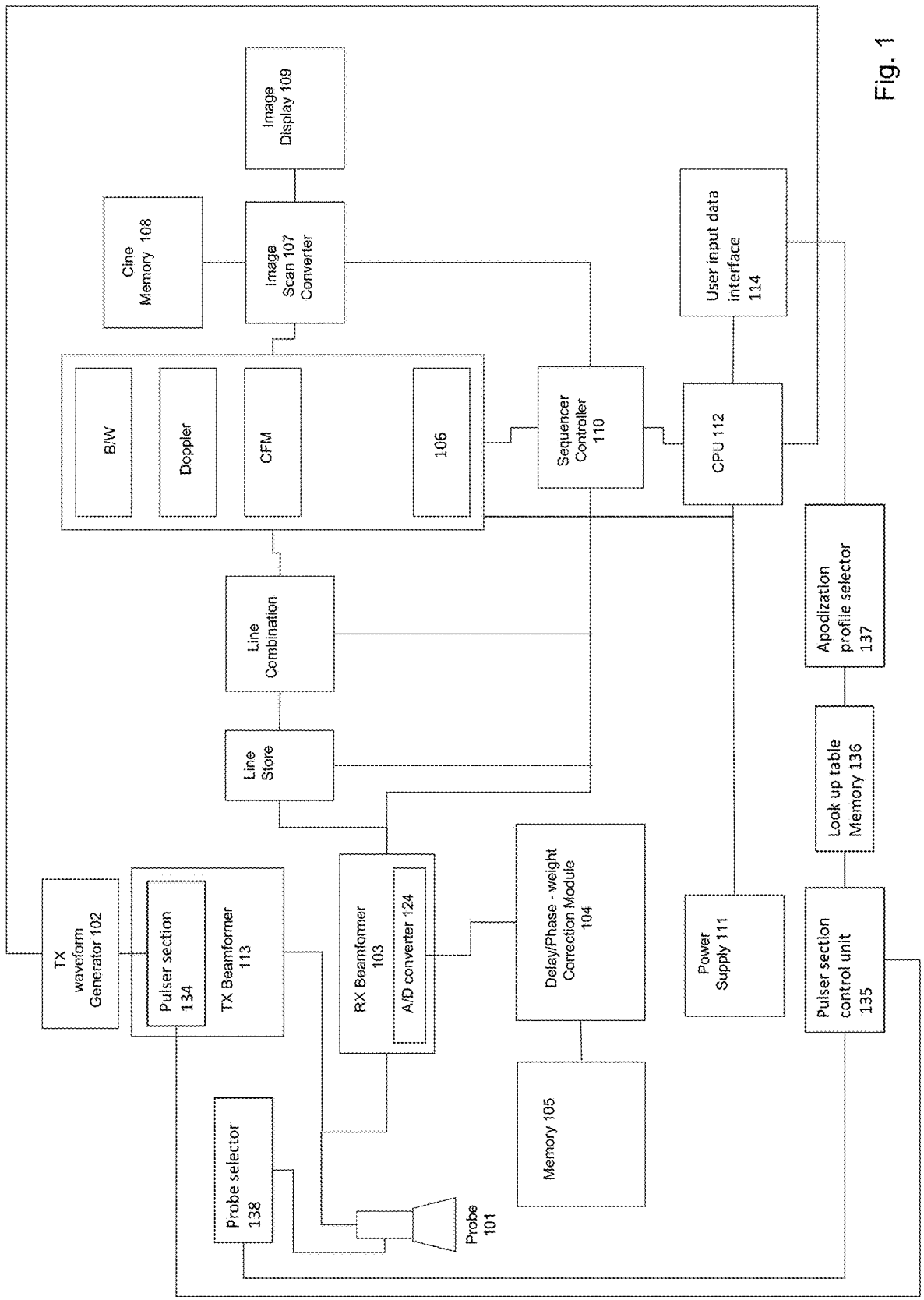
FIG. 1 shows a block diagram of an exemplary embodiment of an ultrasound system according to the present invention.

FIG. 1 illustrates a high-level block diagram of an ultrasound system implemented in accordance with embodiments herein. Portions of the system (as defined by various functional blocks) may be implemented with dedicated hardware, analog and/or digital circuitry, and/or one or more processors operating program instructions stored in memory. Additionally, or alternatively, all or portions of the system may be implemented utilizing digital components, digital signal processors (DSPs) and/or field programmable gate arrays (FPGAs) and the like. The blocks/modules illustrated in FIG. 1 can be implemented with dedicated hardware (DPSs, FPGAs, memories) and/or in software with one or more processors.

The ultrasound system of FIG. 1 includes one or more ultrasound probes 101. The probe 101 may include various transducer array configurations, such as a one dimensional array, a two dimensional array, a linear array, a convex array and the like. The transducers of the array may be managed to operate as a 1D array, 1.25D array, 1.5D array, 1.75D array, 2D array, 3D array, 4D array, etc.

The ultrasound probe 101 is coupled over a wired or wireless link to a receive beamformer (RX) indicated by 103 and to a transmission beamformer (TX) indicated by 113. The TX and RX beamformers may be implemented together or separately. The beamformer 113 supplies transmit signals to the probe 101 and the beamformer 103 performs beamforming of "echo" receive signals that are received by the probe 101.

A TX waveform generator 102 is coupled to the beamformer 103 and generates the transmit signals that are supplied from the beamformer 103 to the probe 101. The transmit signals may represent various types of ultrasound TX signals such as used in connection with B-mode imaging, Doppler imaging, color Doppler imaging, pulse-inversion transmit techniques, contrast-based imaging, M-mode imaging and the like. Additionally, or alternatively, the transmit signals may include single or multi-line transmit, shear wave transmit signals and the like.

The beamformer 113 performs beamforming of the transmit beams in order to focalize the transmit beams progressively along different adjacent lines of sight covering the entire ROI.

According to the present embodiment, the transmit waveform generator provides the settings of the electric excitation signals of the transducer elements of the array of the probe. The said settings are related to parameters as the frequency of the excitation signal, the number of duty cycles of squared wave of which the said signal is composed, the delays to be applied to each excitation signal of each of the transducer elements selected to be excited to emission of an ultrasound signal, in order to cause the said acoustic signals to be focused on a region or on a point located in the target region. Focusing consists in this case to delay the acoustic signals emitted by each transducer element relatively to the other signals emitted by the other acoustic elements in such a way as to cause the said signals to combine constructively at the focus point or at a region to which the ultrasound beam is to be focused.

The signals generated by the waveform generator 102 are fed separately to the corresponding transducer element. The delays are applied in the TX beamformer 113. According to the present embodiment the TX beamformer comprises or is provided in combination with a pulser section 134. This section generates a pulsed electric excitation signal having a certain number of cycles corresponding to a sequence of pulses of certain number of pulses. The pulses have a square waveform and have a predetermined length and a predetermined amplitude.

The pulser section 134 comprises or operates in combination with a modulator which modulates each or at least part of the pulsed electric signals by feeding to the transducer elements only a predetermined portion of the pulses of the said pulsed electric signals.

According to the present embodiment this is carried out by cutting the duration of each pulse of the pulsed electric excitation signal according to a predetermined time period.

According to an embodiment herein the cut off of the pulses of the excitation signals is carried out by shutting off or interrupting the feeding channel of the excitation signal to the corresponding transducer element.

The time period of cutting the duration of each pulse is chosen in such a way to control the overall energy applied to probe's elements so that the acoustic energy field generated by the transmitted ultrasound pulse by the probe is subjected to apodization showing a predetermined profile in which the sidelobes are significatively reduced or suppressed.

Given a certain apodization profile, the pulse cut off periods can be calculated theoretically, selectively for each transducer element or the said cut off periods can be taken from an experimentally generated database in which a certain apodization profile is associated univocally to a certain set of cut off periods. In the present example of FIG. 1, both alternatives are possible.

A pulser control unit 135 is provided which is configured by a control program to operate the pulser section unit 134 as described above. The data relating to the cut off periods of the excitation signals related to each different transducer are taken either from a look up table saved in a memory 136 or this data is inputted by the user through the User input interface 114.

According to a further feature which is provided in the present example, an apodization profile selector 137 may be provided allowing either the user and/or the technicians of the producer to select a certain desired apodization profile of the acoustic wave transmitted by the probe. In this case the look up table may be constructed in such a way as comprising different apodization profiles each one associated with the set of cut off periods of the excitation signals fed to the corresponding transducer elements.

In the case that the apodization profile is factory preset, the pulser section control unit may be configured to automatically find and load the cut off periods related to the set apodization profile.

According to still a further embodiment, which is shown in the example of FIG. 1, but which could also not be provided, the probe 101 can send data to a probe selector 138 when the said probe is connected to the system. According to factory set optimal default settings, the system can automatically select the probe type, the corresponding look up table in the memory 136 and the optimum default apodization profile, thus allowing the pulser section control unit 135 to automatically receive or read the corresponding settings of the cut off periods.

In alternative embodiment, the probe is provided with a memory in which the probe type is saved and which memory can be read by the system at the connection of the probe. The probe selector 138 can thus read automatically the probe type and operate the automatic selection of the optimal default look up table, the default apodization profile and the corresponding default settings of the cut off period.

Further to the transmit beam generation section, the system comprises the receive beamformer 103 performing beamforming upon received echo signals to form beamformed echo signals in connection to pixel locations distributed across the region of interest. For example, in accordance with certain embodiments, the transducer elements generate raw analog receive signals that are supplied to the beamformer. The beamformer adjusts the delays to focus the receive signal along one or more select receive beams and at one or more select depths within the region of interest (ROI). The beamformer adjusts the weighting of the receive signals to obtain a desired apodization and profile. The beamformer applies weights and delays to the receive signals from individual corresponding transducers of the probe. The delayed, weighted receive signals are then summed to form a coherent receive signals.

The beamformer 103 includes (or is coupled to) an A/D converter 124 that digitizes the receive signals at a selected sampling rate. The digitization process may be performed before or after the summing operation that produces the coherent receive signals.

Optionally, a dedicated sequencer/timing controller 110 may be programmed to manage acquisition timing which can be generalized as a sequence of firings aimed at select reflection points/targets in the ROI. The sequence controller 110 manages operation of the TX and the RX beamformer 103, 113 in connection with transmitting ultrasound beams and measuring image pixels at individual LOS locations along the lines of sight. The sequence controller 110 also manages collection of receive signals.

One or more processors 106 perform various processing operations as described herein.

According to an embodiment herein the sequencer 110 controls the beamformer in order to generate and transmit a plurality of transmit beams which are focalized in such a way as to show an aperture or a beam width encompassing a certain number of line of sights or of receive lines. The transmit beams of the said plurality being progressively laterally shifted along the array of transducer elements of the probe and thus along the ROI for scanning the entire ROI. A certain line of sight or a certain receive line will be encompassed by a certain number of different transmit beam of the said plurality as long as the said line of sight position or the said receive line position falls within the aperture of the said transmit beams or within the width of the said transmit beams. Thus for a reflecting point on a certain receive line or line of sight having a certain line position within the ROI and relatively to the transducer array of the probe a certain number of receive signals contributions are received each one deriving from a different transmit beam whose center transmit line having different lateral shifts relatively to the said reflecting point and to the corresponding receive line.

The receive data relatively to the echoes from the said reflecting point is a combination of the contributions of the receive signals from the said reflecting point deriving from the said certain number of transmit beams.

In accordance with embodiments herein, the beamformer 103 includes an input that is configured to be coupled to an ultrasound probe 101 and receive signals from transducers of the ultrasound probe 101. The memory 105 stores time delays to align contributions of reflection signals received by the transducers of the array of the probe 101 from the reflectors in the ROI. The memory 105 also stores phase corrections to correct phase differences of the receive signals contributions for each transducer element and deriving from each of the said certain number of differently laterally shifted transmit beams relatively to the receive line or line of sight on which the said reflector point is located.

A delay/phase correction (DPC) module 104 is coupled to the memory 105 and provides various delays and corrections to the beamformer 103. For example, the DPC module 104 directs the beamformer 103 to apply time delay and phase correction to the receive signals to form delayed receive signals. The beamformer 103 then sums, in a coherent manner, the delayed receive signals to obtain a coherent receive signal in connection with a reflection point or a reflection target.

Optionally, the memory 105 may store a common phase shift correction in connection with multiple channels. Different phase shift corrections may be stored in connection with various corresponding channels in the case of multiple receive signals are received along a common receive line position but due to a certain number of different transmit beams each one having a laterally shifted transmit center line and an aperture or width encompassing the receive line position. The memory 105 may also store weights such as apodization weights and/or RTB weights.

As explained herein, the beamformer 103 (circuitry) is configured to apply contemporaneously to each receive signal contribution of each transducer element from a reflection point a beamforming focalization delay and a phase shift equalization delay so called RTB delay. The said beamforming focalization delay being calculated basing on the time of arrival of the said signal contribution to a transducer element when traveling from the reflection point to the said transducer element and the said phase shift equalization delay being determined according to the difference in phase of the wave front reaching the reflecting point relatively to the phase of the wave fronts reaching the same reflecting point and being of further transmitted beams which are laterally shifted each other.

Optionally, the memory 105 may store a pre-calculated table, where the pre-calculated table comprises real times of arrival of the receive signals relative to a predetermined reflection point. Optionally, the processor 106 may be configured to calculate real times of arrival of the receive signals relative to a predetermined reflection point. Optionally the memory 105 may store a pre-calculated table, where the pre-calculated table comprises pre-calculated phase shift equalization delays to be applied contemporaneously to the beamforming focalization delays to the receive signals of a receive line along a certain line of sight or a certain receive line position deriving from a certain number of transmit beams being differently laterally shifted relatively to the said receive line position, the number of the said transmit beams being set by setting a certain aperture or lateral width of the said transmit beams. Optionally the memory 105 may store a pre-calculated table of the said phase shift equalization delays which are pre-calculated for one or more of different transmit beams apertures or widths.

Optionally, the processor 106 may be configured to calculate the said phase shift equalization delays for one or more of different transmit beams apertures or widths.

Optionally, the beamformer 103 circuitry may further comprise an adder unit for adding the beamforming delays and the phase shift equalization delays (RTB delays) for the receive signal contributions deriving from each reflecting point.

In accordance with certain embodiments, at least a portion of the beamforming process may be implemented by the processor 106 (e.g., in connection with software RTB beamforming). For example, the memory 105 may store beamforming related program instructions that are implemented by the processor 106 to contemporaneously apply beamforming delays and phase shift equalization delays to the receive signals.

The processor 106 and/or CPU 112 also performs conventional ultrasound operations. For example, the processor 106 executes a B/W module to generate B-mode images. The processor 106 and/or CPU 112 executes a Doppler module to generate Doppler images. The processor executes a Color flow module (CFM) to generate color flow images. The processor 106 and/or CPU 112 may implement additional ultrasound imaging and measurement operations.

Optionally, the processor 106 and/or CPU 112 may filter the first and second displacements to eliminate movement-related artifacts.

An image scan converter 107 performs scan conversion on the image pixels to convert the format of the image pixels from the coordinate system of the ultrasound acquisition signal path (e.g., the beamformer, etc.) and the coordinate system of the display. For example, the scan converter 107 may convert the image pixels from polar coordinates to Cartesian coordinates for image frames.

A cine memory 108 stores a collection of image frames over time. The image frames may be stored formatted in polar coordinates, Cartesian coordinates or another coordinate system.

An image display 109 displays various ultrasound information, such as the image frames and information measured in accordance with embodiments herein. The display 109 displays the ultrasound image with the region of interest shown.

A control CPU module 112 is configured to perform various tasks such as implementing the user/interface and overall system configuration/control. In case of fully software implementation of the ultrasound signal path, the processing node usually hosts also the functions of the control CPU.

A power supply circuit 111 is provided to supply power to the various circuitry, modules, processors, memory components, and the like. The power supply 111 may be an A.C. power source and/or a battery power source (e.g., in connection with portable operation).

Figure 2:
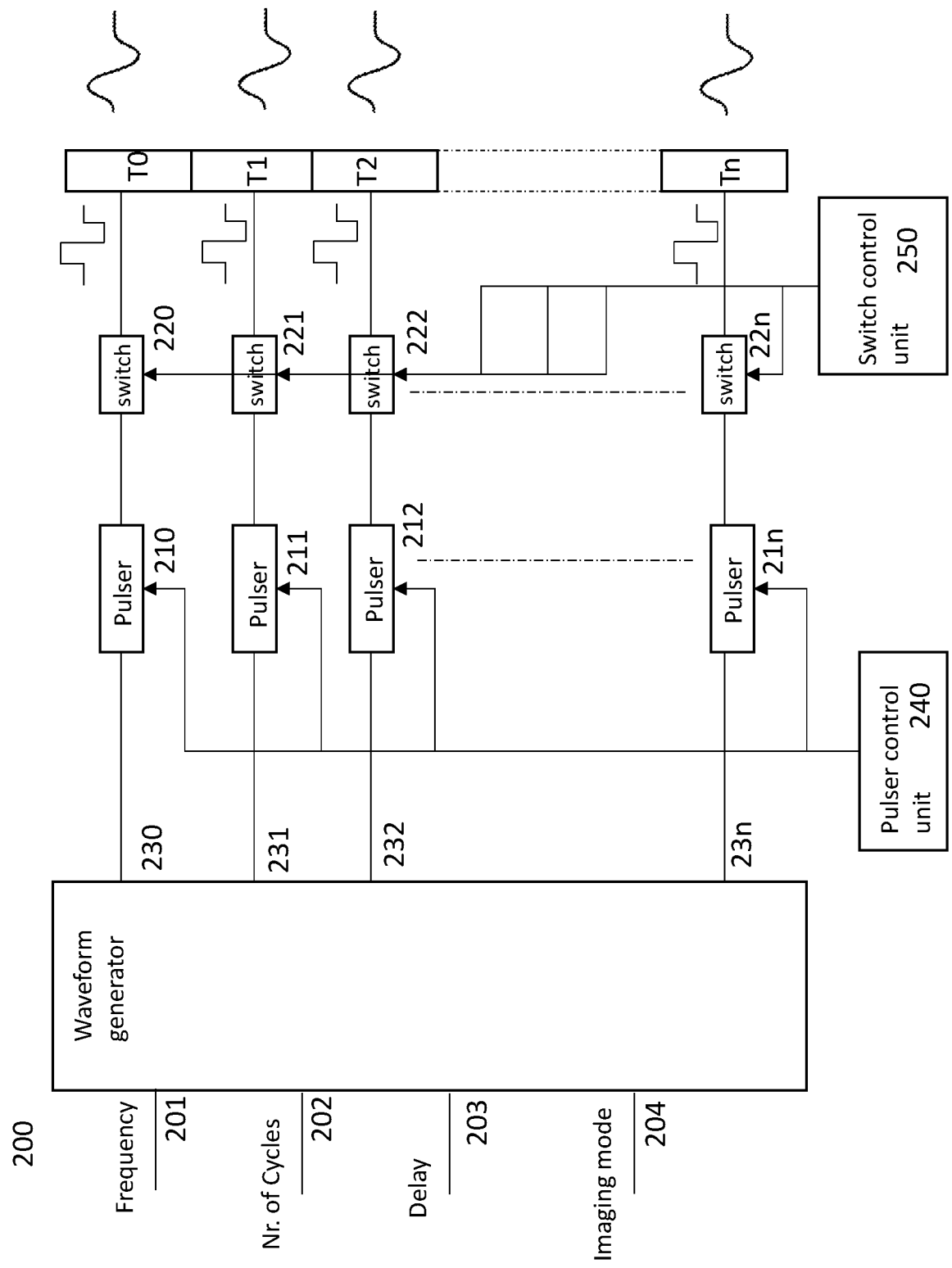
FIG. 2 show an exemplary embodiment of the section for generating the ultrasound transmit beam according to the present invention.

FIG. 2 illustrates an embodiment of the wave form generator and of the pulser section which for example can be provided in the system according to the previous example of FIG. 1 or in similar ultrasound system having different architectures.

As in conventional ultrasound systems, the transmitting function is carried out by a subsystem comprising a probe with a transducer array. The transducer array is formed by a predefined number of individual transducer elements T0, T1, T2, . . . , Tn that convert electronic signals into acoustic energy and vice versa.

Although the transducer array shown in FIG. 2 is for simplicity sake a so called linear array in which the transducer elements T1, to Tn are placed one beside the other and distributed along a rectilinear line, the teaching of the present embodiment and of the invention can be provided, mutatis mutandis, in combination with different transducer array configurations, such as a one dimensional array, a two dimensional array, a linear array, a convex array and the like. The transducers of the array may be managed to operate as a 1D array, 1.25D array, 1.5D array, 1.75D array, 2D array, 3D array, 4D array, etc.

A waveform generator 200 produces a driving waveform which is fed by dedicated feeding lines 230, 231, 232, . . . , 23n separately to each of the transducer elements T0 to Tn.

Alternatively, the number of feeding lines can be less than the number of the transducer elements and each line is connected alternatively to two or more different transducer elements by means of multiplexing or other kind of switches.

The waveform generator 200 produces a digital representation of the electric excitation signal of the transducer elements. This electric excitation signal being a pulsed one and comprising a sequence of pulses. By the waveform generator the said excitation signals and the pulses are defined by a number of parameters including its frequency, the number of cycles, i.e. the number of pulses in the sequence, and its delay. Delays can be calculated or read from a look up table according to a focusing rule of the single acoustic signal contributions emitted by the single transducer elements at a focusing point or region in the target body. The focusing rules being set according to a well-known technology which is part of the common technical knowledge of the skilled person.

According to the shown exemplary embodiment, the waveform generator 200 can receive or read the said settings about the frequency of the excitation signal, the number of cycles, the delays, and also the imaging mode for which the ultrasound pulses has to be applied and the data is fed or received for example by input ports 201, 202, 203, 204.

The digital representation generated by the waveform generator 200 is converted into an analog waveform by the pulsers 210, 211, 21n. In the case of a bipolar pulser, the pulsers are supplied with a positive and negative reference voltage by a pulser control unit 240. The digital representation specifies at each instant of time whether the output should be 0, the positive reference voltage, or the negative reference voltage.

According to an embodiment, the same reference voltage is supplied to all of the pulsers 210, 211, 212, . . . , 21n.

In the present example, each feeding line 230, 231, 232, . . . , 23n is provided with a dedicated pulser 210, 211, 212, . . . , 21n.

Variant embodiment may be provided in which the pulser is a common pulser for all the feeding lines 230, 231, 232, . . . , 23n or for part of the said feeding lines.

In each feeding line 230, 231, 232, . . . , 23n a pulse energy modulator is provided which operates in the sense of reducing selectively the energy of the pulses emitted by each of the transducer elements T0, T1, T2, . . . , Tn. Energy reduction is applied in a different manner for the different transducer elements in such a way as to apply a certain predefined apodization profile to the transmitted ultrasound wave i.e. in such a way as to suppress sidelobes in the acoustic energy distribution profile of the transducer array.

Considering the present example of a linear array of transducer, the modulation of the acoustic energy emitted by the single transducer elements T0 to Tn, is set symmetrically in relation to a central transducer element of the array or to the central propagation axis of the ultrasound wave, the energy of the acoustic ultrasound signal emitted by each transducer element positioned laterally relatively to the said central one or to the said central axis of the ultrasound wave emitted by the array of transducers reduces according to a predefined value as a function of the position of each transducer relatively to the said central one or to the said central axis. The said variation of the acoustic energy is obtained by correspondingly varying the energy of the pulsed signal or of each of the pulses of the electric excitation signals of the transducer arrays.

Many different functions may be set for determining the said variation of the pulse energy. The optimization of the said functions can be obtained by theoretical calculation, simulating the total energy distribution of the ultrasound wave emitted by the array as a function of the position of the transducers as it will appear more clearly from FIGS. 4a to 4c.

As already disclosed in combination with the example of FIG. 1, the said functions or the optimization of the function of the variation of the energy of the pulsed of the excitation signals driving each transducer element may be determined experimentally, by measuring the acoustic energy distribution as a function of the transducer position, i.e. the apodization profile of the ultrasound wave emitted by the entire array of transducers.

For a given configuration of transducer array, or for a certain type of probe provided with an array having a certain configuration, a look up table can be generated in which the different apodization profiles can be univocally related to the said function determining the variation of the pulse energy of the excitation signals of the different transducer elements of the array. This look up table can be generated one for a given probe and for a given ultrasound system as a factory determined configuration tool and can be saved in a memory which can be read by the control unit of the transmit section of the ultrasound system and used by the said transmit section for generating the ultrasound transmission beam.

According to a further feature of the present embodiment of FIG. 2, the energy of the pulsed of each of the excitation signals of the different transducer elements is varied by varying a cut off period of the pulsed signal or of each pulse forming the said pulsed signal. This is obtained by interrupting the feeding line to each of the transducer elements for a predetermined feeding line shut off period, the said shut off period reducing the pulse energy to the value defined by one of the above functions.

In the present embodiment, in each feeding line 230, to 23n, there is provided a switch 220, 221, 222, . . . , 22n. Each switch having to alternative conduction status namely open or closed and each switch being independently controlled by a switch control unit 250. The switch control unit 250 changing the status of the switch from open to closed, maintaining the open status for the shut off period provided for the corresponding transducer element T0 to Tn of the array of transducers.

Figures 3A, 3B, 3C:
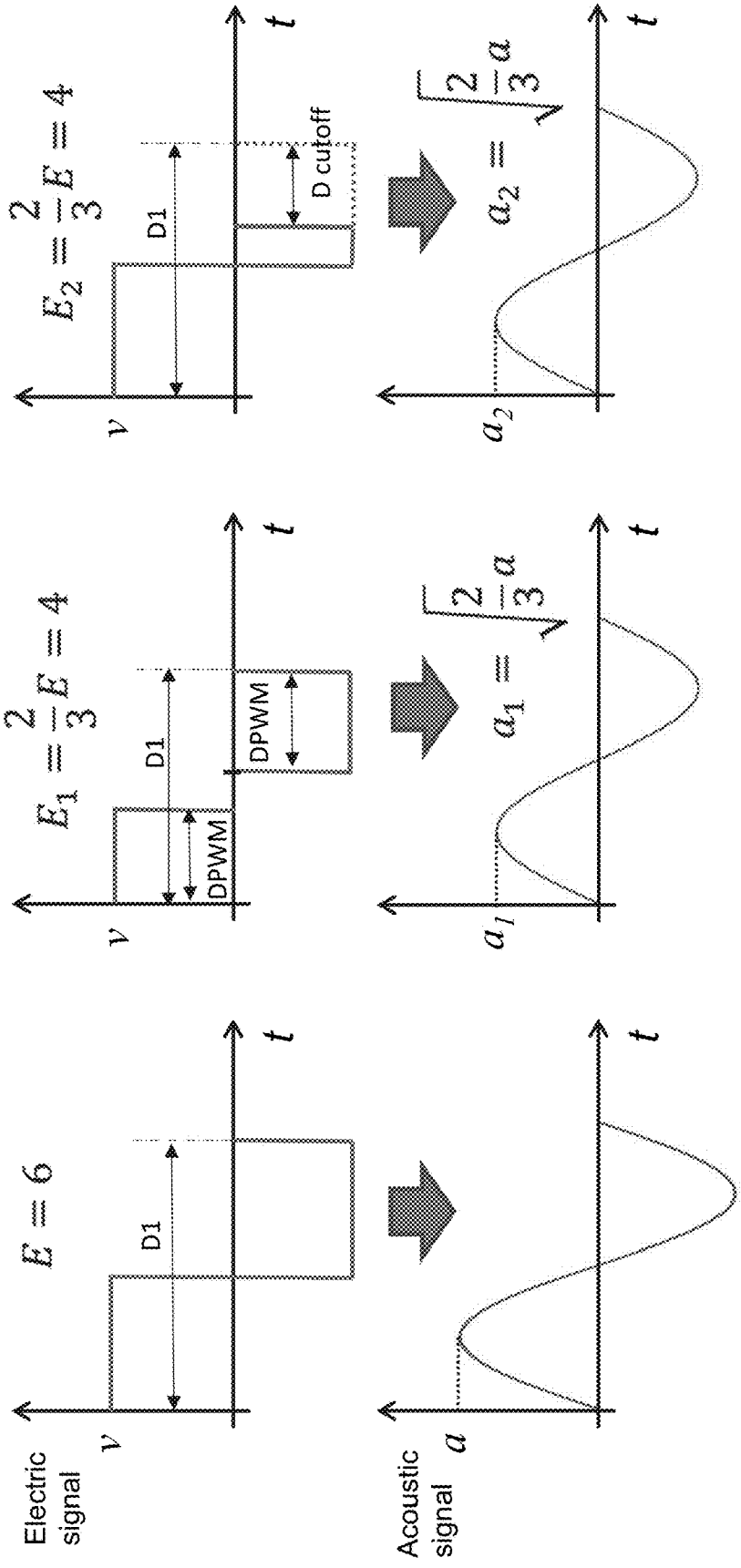
FIG. 3a shows one period of the pulse of the pulsed excitation signal generated by a pulser without any apodization and the corresponding acoustic signal transmitted by a transducer excited by the said signal.
FIG. 3b shows one period of the pulse of the pulsed excitation signal generated by a pulser which pulse is modulated by means of a Pulse Width Modulation (PWM) and the corresponding acoustic signal transmitted by a transducer excited by the said signal.
FIG. 3c shows one period of the pulse of the pulsed excitation signal generated by a pulser with the pulse modulated by means of the method according to the present invention and the corresponding acoustic signal transmitted by a transducer excited by the said signal.

FIG. 3a to FIG. 3c shows the principle of the present invention in comparison to the condition where no apodization is applied to the ultrasound wave transmitted by the array and where the pulse energy is varied by using a Pulse width Modulation according to the state of the art. For each case a pulse of the pulse sequence of the electric excitation signal is shown and the corresponding acoustic signal emitted by a transducer element fed with the said electric signal. The pulse is represented by the voltage value as a function of time, while the acoustic signal shows the amplitude in relation to time.

The pulse cycle or period in the three cases is indicated as D1. As it appears using the Pulse width Modulation approach, the pulse width of each semi period is modified as indicated by DPWM in the sense that the pulse width is shortened in relation to the complete duration of the half period as in the case in which no apodization is applied.

In the present case assuming an energy of the pulse to which no apodization is applied as E=6, using the Pulse Width Modulation and shortening the duration of each pulse in each half period of an amount corresponding to ⅓ the total energy of each pulse is reduced to 4.

Setting the amplitude as a for the pulse of the case where no apodization is applied then in the case using the Pulse width Modulation approach the amplitude of the acoustic signal is a1 and corresponds to a value of $\sqrt{\frac{2}{3}a}$.

The third case corresponds to the method according to the present invention. As it appears from the graph representing the electric signal each pulse is simply cut off for a certain length, namely for a certain cut off duration which is indicated as Dcutoff in FIG. 3c. also in this case the duration of the cut off is set of such length that the total energy of the pulse is of ⅔ of E, (E being the total energy of the pulse in the case where no apodization is applied). The corresponding acoustic signal generated by a transducer element fed with the above electric signal is illustrated in the lower graph of FIG. 3C and as it is indicated the amplitude a2 has the same value as in the case of the example of FIG. 3b applying apodization according to the Pulse Width Modulation approach.

Figure 4C:
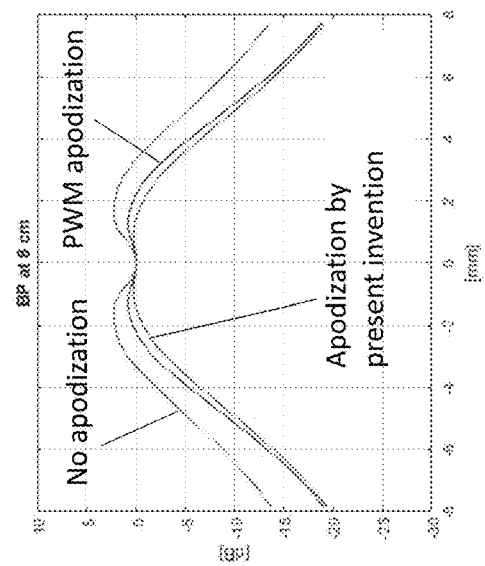
FIG. 4a to FIG. 4C shows the acoustic energy field simulations of the ultrasound wave generated by a linear transducer array at different depth, i.e. different distances from the transducer surface in the case of no apodization, apodization using Pulse width modulation and apodization by means of the method according to the present invention.
Figure 4B:
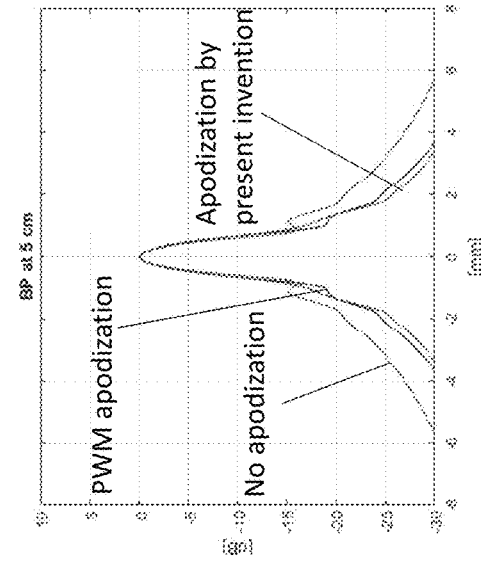
Figure 4A:
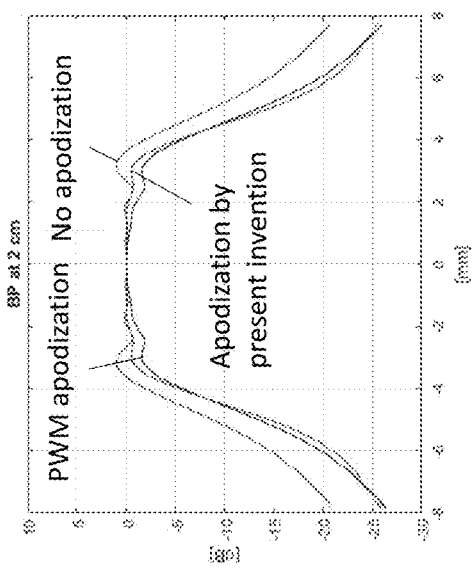

FIGS. 4a to 4c show the results of the simulation of the acoustic energy distribution along the extension of a linear array of transducers setting the zero position coincident with the center line of a central transducer or the centerline of the array of transducers. Each of the figures represents the acoustic energy distribution of an ultrasound wave emitted by a linear array of transducers at different propagation depth of the ultrasound beam in a target region. The three profiles relate to the case where no apodization is applied, the case where an apodization method is applied using the Pulse Width Modulation approach indicated by PWM apodization and where the apodization is carried out according to the teaching of the present invention. It appears clearly that the method of the present invention provides results which are close to the ones obtained with the current Pulse Width Modulation approach. These results are obtained using a simpler technique which can be carried out by less hardware and by simpler operating units.

According to a further advantage, differently from the prior art methods and systems, there is no need to operate at the level of the waveform generator or of the pulser which may be the set in the same way for each of the transducer elements. The energy reduction of the acoustic signals contributing to the acoustic wave generated by the array of transducers can be simply modified as a function of the position of the corresponding transducer element in the array by setting a predefined shut off period of the channel, and particularly a predefined period of interruption of the feeding line of the corresponding transducer.

A particular method for generating an ultrasound transmission wave by an ultrasound system as for example the system disclosed according to FIG. 1, is described in combination with the flow diagram of FIG. 5.

Said flow diagram is referred to an embodiment in which the cut off periods of the pulses of the electric excitation signals of the different transducer elements are registered in a look up table which is generated for a specific array of transducers or a specific probe and related of a specific apodization profile, i.e. acoustic energy distribution profile, of the emitted ultrasound wave. In this case two phase are provided a first phase for constructing the look up table and a second phase relating to the use of the said look up table for generating an ultrasound transmission wave or beam. The two phases being separated by a dotted line in FIG. 5.

Phase I is the look up table generation phase. This phase can be executed any time when using a certain type of probe after having connected the probe to the ultrasound system and before executing the imaging session or it can be executed in a different time, before carrying out the imaging session. In this case the said phase I can be executed only once for each type of probe or for each combination of a type of probe and a certain type of ultrasound system. The look up table is then stored in a memory in the electronic circuits of the ultrasound system and the data are furnished or can be read by the transmit wave generation section.

According to the embodiment of FIG. 5, in phase one at step 500 the probe is connected to a sample ultrasound system and the ultrasound transmission wave generating section is driven to generating an excitation pulse or a sequence of excitation pulses of a transducer element for selected transducer elements of a transducer array. This is executed as indicated at step 501 by defining a preset shut off time of the feeding line of the corresponding transducer element for at least one or for more of the transducer elements selected from the transducer elements of the array or for all the said transducer elements. At step 502 the excitation pulse or the sequence of excitation pulses is fed to the corresponding transducer element for a preset standard time, i.e maintaining the feeding line conductive for the said preset standard time. Step 503 consists in measuring the apodization profile, i.e. the energy distribution profile of the ultrasound wave emitted by the array of transducers with the settings defined at the previous steps.

Step 504 provides for Saving the data pairs relating to the excitation pulse, the preset standard time and the preset shut off time for each transducer element and the corresponding measured apodization profile of the emitted ultrasound wave.

As indicated at step 505 if further pre-set shut off times are provided or needed the process is prosecuted as indicated at step 506. At this step, for at least one or for more of the transducer elements a further different preset of shut off times of the feeding line of the corresponding transducer element is defined. These preset times are used for repeating the steps 500 to 505.

When no further sets of shut off periods are requested or provided, the process prosecutes with step 507 providing to generate a look-up table of apodization profiles in relation to the shut off times of the at least part of the transduce elements during TX. The said look up table is then saved in the ultrasound system control unit as indicated by step 508.

Phase II relates to the carrying out of an ultrasound imaging session and especially of generating the ultrasound transmission wave. A probe is connected to a system as indicated with step 509, the system being provided with a look up table saved in a memory and the look up table having been generated according to the phase I.

Upon connection of the probe to the system a step 510 is carried out. In this case, two alternatives which can be both provided in the same ultrasound system and which in this case can be activated alternatively are possible. According to a first alternative, the ultrasound system is configured to automatically recognize the type of ultrasound probe and to automatically select the corresponding look up table and automatically apply the set of shut off times of each channel of the probe according to the desired apodization profile by reading the data from look up table.

According to a second alternative the type of the probe has to be set manually by the user by means of a user interface providing with a probe type selection routine and probe type selection input organs. Following the manual probe selection the steps of selection the corresponding look up table and applying the set of shut off times of each channel of the probe according to the desired apodization profile by reading the data from look up table can be carried out at least in part automatically or as an alternative the said steps of selection the corresponding look up table and applying the set of shut off times of each channel of the probe according to the desired apodization profile by reading the data from look up table can be carried out at least in part manually. In this case the different alternatives can be offered to selection by the user in selection menus or the like.

When step 510 is terminated the said set of shut off times are used to drive the transducer elements of the probe as indicated at step 511.

Figure 6:
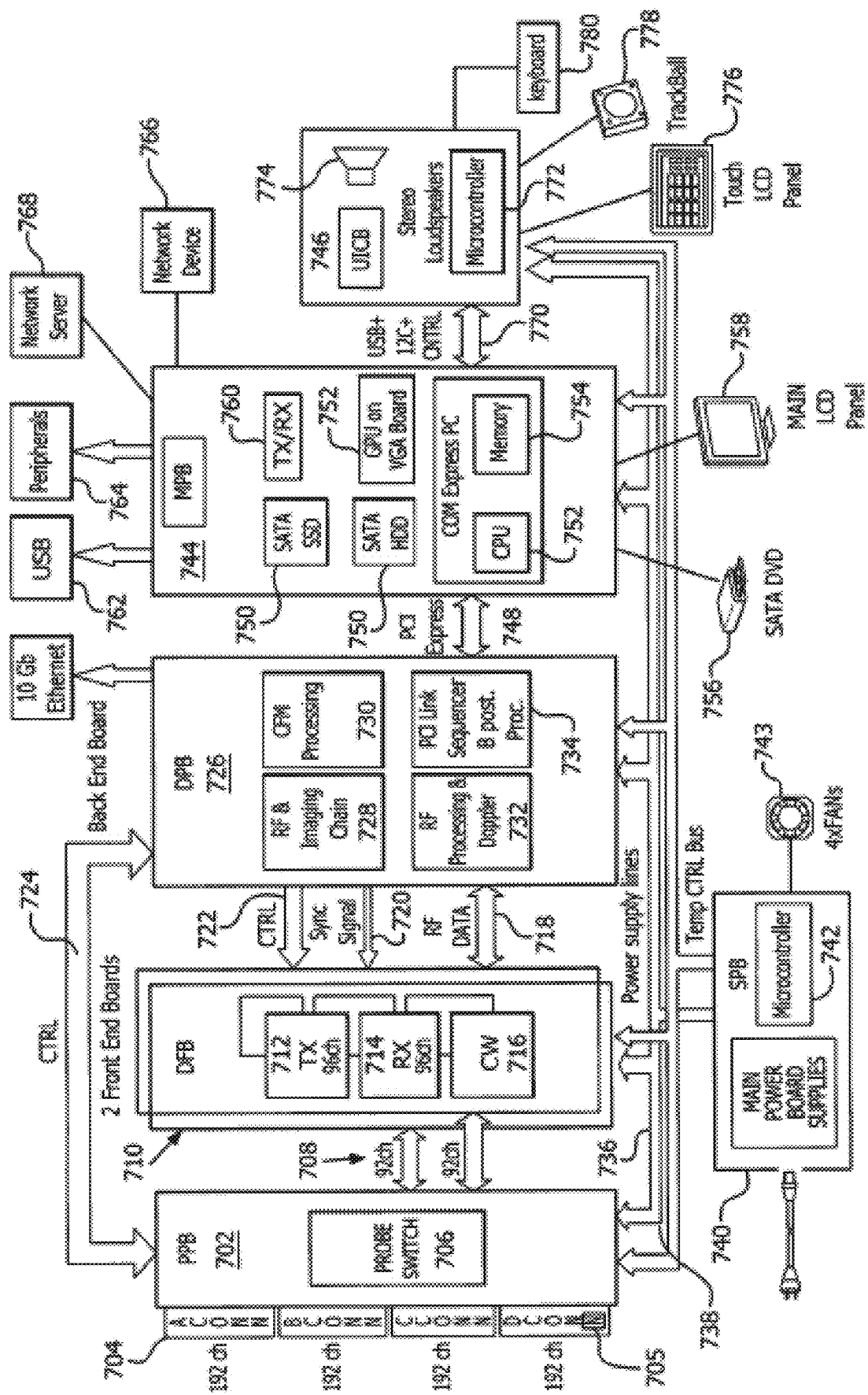
FIG. 6 illustrates a block diagram of an ultrasound system formed in accordance with an alternative embodiment.

FIG. 6 illustrates a block diagram of an ultrasound system formed in accordance with an alternative embodiment. The system of FIG. 6 implements the operations described herein in connection with various embodiments. By way of example, one or more circuits/processors within the system implement the operations of any processes illustrated in connection with the figures and/or described herein. The system includes a probe interconnect board 602 that includes one or more probe connection ports 704. The connection ports 604 may support various numbers of signal channels (e.g., 128, 192, 256, etc.). The connector ports 704 may be configured to be used with different types of probe arrays (e.g., phased array, linear array, curved array, 1D, 1.25D, 1.5D, 1.75D, 2D array, etc.). The probes may be configured for different types of applications, such as abdominal, cardiac, maternity, gynecological, urological and cerebrovascular examination, breast examination and the like.

One or more of the connection ports 604 may support acquisition of 2D image data and/or one or more of the connection ports 604 may support 3D image data. By way of example only, the 3D image data may be acquired through physical movement (e.g., mechanically sweeping or physician movement) of the probe and/or by a probe that electrically or mechanically steers the transducer array.

The probe interconnect board (PIB) 602 includes a switching circuit 606 to select between the connection ports 604. The switching circuit 606 may be manually managed based on user inputs. For example, a user may designate a connection port 604 by selecting a button, switch or other input on the system. Optionally, the user may select a connection port 604 by entering a selection through a user interface on the system.

Optionally, the switching circuit 606 may automatically switch to one of the connection ports 604 in response to detecting a presence of a mating connection of a probe. For example, the switching circuit 606 may receive a "connect" signal indicating that a probe has been connected to a selected one of the connection ports 604. The connect signal may be generated by the probe when power is initially supplied to the probe when coupled to the connection port 604. Additionally, or alternatively, each connection port 604 may include a sensor 605 that detects when a mating connection on a cable of a probe has been interconnected with the corresponding connection port 604. The sensor 605 provides signal to the switching circuit 606, and in response thereto, the switching circuit 606 couples the corresponding connection port 604 to PIB outputs 608. Optionally, the sensor 605 may be constructed as a circuit with contacts provided at the connection ports 604. The circuit remains open when no mating connected is joined to the corresponding connection port 604. The circuit is closed when the mating connector of a probe is joined to the connection port 604.

A control line 624 conveys control signals between the probe interconnection board 602 and a digital processing board 624. A power supply line 636 provides power from a power supply 640 to the various components of the system, including but not limited to, the probe interconnection board (PIB) 602, digital front end boards (DFB) 610, digital processing board (DPB) 626, the master processing board (M PB) 644, and a user interface control board (UI CB) 646. A temporary control bus 638 interconnects, and provides temporary control signals between, the power supply 640 and the boards 602, 610, 626, 644 and 646. The power supply 640 includes a cable to be coupled to an external AC power supply. Optionally, the power supply 640 may include one or more power storage devices (e.g. batteries) that provide power when the AC power supply is interrupted or disconnected. The power supply 640 includes a controller 642 that manages operation of the power supply 640 including operation of the storage devices.

Additionally, or alternatively, the power supply 640 may include alternative power sources, such as solar panels and the like. One or more fans 643 are coupled to the power supply 640 and are managed by the controller 642 to be turned on and off based on operating parameters (e.g. temperature) of the various circuit boards and electronic components within the overall system (e.g. to prevent overheating of the various electronics).

The digital front end boards 610 include transmit driver circuits 612 that generate transmit signals that are passed over corresponding channels to the corresponding transducers in connection with ultrasound transmit firing operations. The transmit driver circuits 612 provide pulse or control for each drive signal and transmit beamforming management to steer firing operations to points of interest within the region of interest. By way of example, a separate transmit driver circuits 612 may be provided in connection with each individual channel, or a common transmit driver circuits 612 may be utilized to drive multiple channels. The transmit driver circuits 612 cooperate to focus transmit beams to one or more select points within the region of interest. The transmit driver circuits 612 may implement single line transmit, encoded firing sequences, multiline transmitter operations, generation of shear wave inducing ultrasound beams as well as other forms of ultrasound transmission techniques.

The digital front end boards 610 include receive beamformer circuits 614 that received echo/receive signals and perform various analog and digital processing thereon, as well as phase shifting, time delaying and other operations in connection with beamforming. The beam former circuits 614 may implement various types of beamforming, such as single-line acquisition, multiline acquisition as well as other ultrasound beamforming techniques.

The digital front-end boards 616 include continuous wave Doppler processing circuits 616 configured to perform continuous wave Doppler processing upon received echo signals. Optionally, the continuous wave Doppler circuits 616 may also generate continuous wave Doppler transmit signals.

The digital front-end boards 610 are coupled to the digital processing board 626 through various buses and control lines, such as control lines 622, synchronization lines 620 and one or more data bus 618. The control lines 622 and synchronization lines 620 provide control information and data, as well as synchronization signals, to the transmit drive circuits 612, receive beamforming circuits 614 and continuous wave Doppler circuits 616. The data bus 618 conveys RF ultrasound data from the digital front-end boards 610 to the digital processing board 626. Optionally, the digital front-end boards 610 may convert the RF ultrasound data to I, Q data pairs which are then passed to the digital processing board 626.

The digital processing board 626 includes an RF and imaging module 628, a color flow processing module 630, an RF processing and Doppler module 632 and a PCI link module 634. The digital processing board 626 performs RF filtering and processing, processing of black and white image information, processing in connection with color flow, Doppler mode processing (e.g. in connection with polls wise and continuous wave Doppler). The digital processing board 626 also provides image filtering (e.g. speckle reduction) and scanner timing control. The digital processing board 626 may include other modules based upon the ultrasound image processing functionality afforded by the system.

The modules 628-634 comprise one or more processors, DSPs, and/or FPGAs, and memory storing program instructions to direct the processors, DSPs, and/or FPGAs to perform various ultrasound image processing operations. The RF and imaging module 628 performs various ultrasound related imaging, such as B mode related image processing of the RF data. The RF processing and Doppler module 632 convert incoming RF data to I,Q data pairs, and performs Doppler related processing on the I, Q data pairs. Optionally, the imaging module 628 may perform B mode related image processing upon I, Q data pairs. The CFM processing module 630 performs color flow related image processing upon the ultrasound RF data and/or the I, Q data pairs. The PCI link 634 manages transfer of ultrasound data, control data and other information, over a PCI express bus 648, between the digital processing board 626 and the master processing board 644.

The modules 628-634 comprise one or more processors, DSPs, and/or FPGAs, and memory storing program instructions to direct the processors, DSPs, and/or FPGAs to perform various ultrasound image processing operations. The RF and imaging module 628 performs various ultrasound related imaging, such as B mode related image processing of the RF data. The RF processing and Doppler module 632 convert incoming RF data to I, Q data pairs, and performs Doppler related processing on the I, Q data pairs. Optionally, the imaging module 628 may perform B mode related image processing upon I, Q data pairs. The CFM processing module 730 performs color flow related image processing upon the ultrasound RF data and/or the I, Q data pairs. The PCI link 634 manages transfer of ultrasound data, control data and other information, over a PCI express bus 648, between the digital processing board 626 and the master processing board 644.

The network devices 666 may represent portable or desktop devices, such as smart phones, personal digital assistants, tablet devices, laptop computers, desktop computers, smart watches, ECG monitors, patient monitors, and the like. The master processing board 644 conveys ultrasound images, ultrasound data, patient data and other information and content to the network devices for presentation to the user. The master processing board 644 receives, from the network devices 666, inputs, requests, data entry and the like.

The network server 668 may represent part of a medical network, such as a hospital, a healthcare network, a third-party healthcare service provider, a medical equipment maintenance service, a medical equipment manufacturer, a government healthcare service and the like. The communications link to the network server 668 may be over the Internet, a private intranet, a local area network, a wide-area network, and the like.

The master processing board 644 is connected, via a communications link 670 with a user interface control board 646. The communications link 670 conveys data and information between the user interface and the master processing board 644. The user interface control board 646 includes one or more processors 672, one or more audio/video components 674 (e.g. speakers, a display, etc.). The user interface control board 646 is coupled to one or more user interface input/output devices, such as an LCD touch panel 676, a trackball 678, a keyboard 680 and the like. The processor 672 manages operation of the LCD touch panel 676, as well as collecting user inputs via the touch panel 676, trackball 678 and keyboard 680, where such user inputs are conveyed to the master processing board 644 in connection with implementing embodiments herein.

In relation to this embodiment of an ultrasound system, it has to be noted that although the channels or the feeding lines of the transducer elements of the array of the probe are not provided with a switch opening and closing the line, the functions of this switches can be carried out not by hardware such as the said switches but by one or more of the processing units provided in the transmit beam generation section which are configured by a program to carry out the functions of the said switches. The said program comprising the instructions to configure the processing units as switches operating according to the method of the present invention as described in the previous embodiments.

Figure 7:
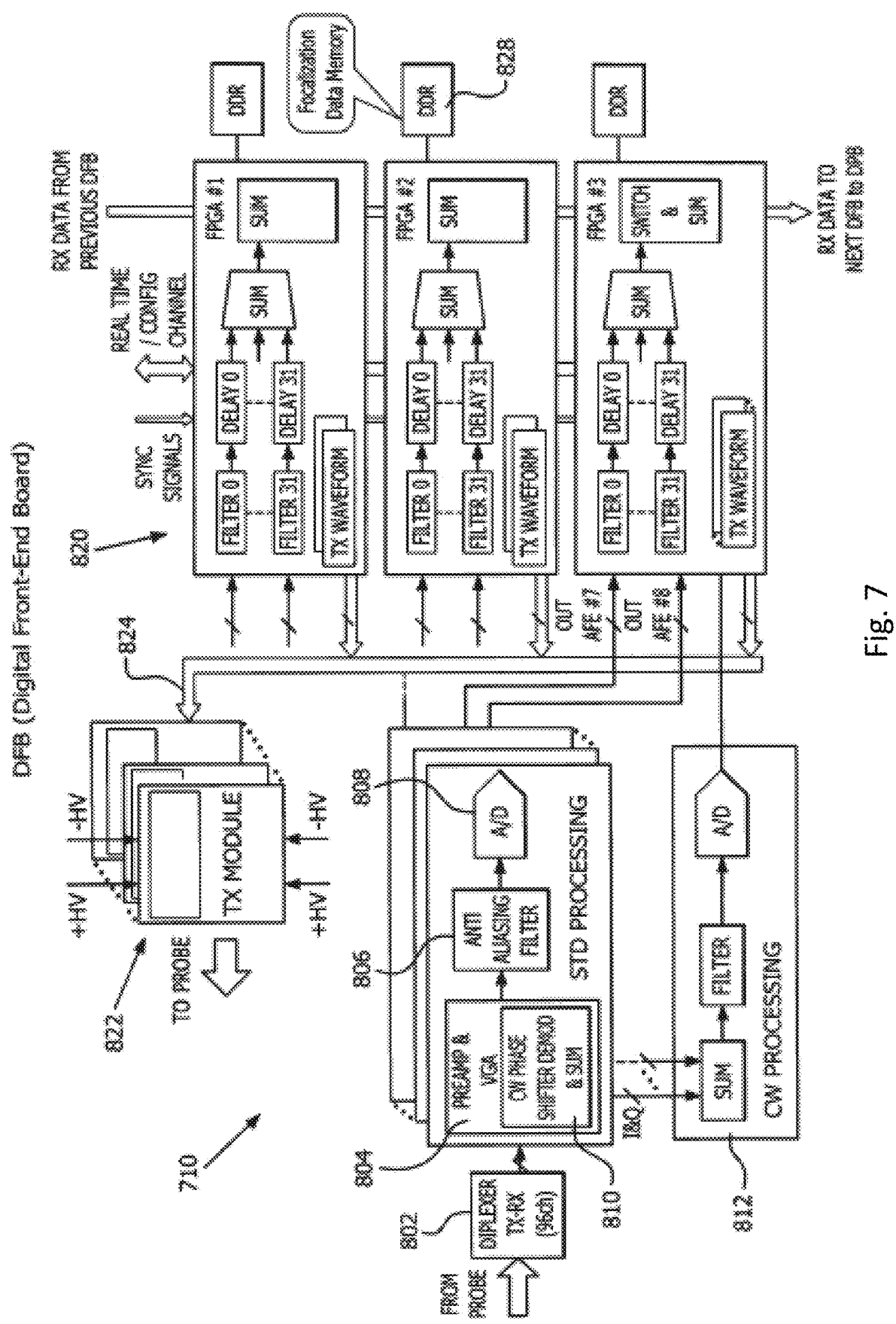
FIG. 7 illustrates a block diagram of a portion of the digital front-end boards.

FIG. 7 illustrates a block diagram of a portion of the digital front-end boards 610 formed in accordance with embodiments herein. A group of diplexers 702 receive the ultrasound signals for the individual channels over the PIB output 708. The ultrasound signals are passed along a standard processing circuit 705 or to a continuous wave processing circuit 712, based upon the type of probing utilized. When processed by the standard processing circuit 705, a preamplifier and variable gain amplifier 704 process the incoming ultrasound receive signals that are then provided to an anti-aliasing filter 706 which performs anti-aliasing filtering.

According to an embodiment the retrospective transmit beam focusing according to the present invention may be applied to the RF data directly acquired by the system or to transformed data according to different transformations as for example as a phase/quadrature (I/Q) transformation, or similar.

In the embodiment of FIG. 7 an example of the said transformation of the RF data is disclosed According to this example, the output of the filter 706 is provided to an A/D converter 708 that digitizes the incoming analog ultrasound receive signals. When a continuous wave (CW) probe is utilized, the signals therefrom are provided to a continuous wave phase shifter, demodulator and summer 710 which converts the analog RF receive signals to I, Q data pairs. The CW I, Q data pairs are summed, filtered and digitized by a continuous wave processing circuit 712. Outputs from the standard or continuous wave processing circuits 705, 712 are then passed to beam forming circuits 820 which utilize one or more FPGAs to perform filtering, delaying and summing the incoming digitized receive signals before passing the RF data to the digital processing board 726 (FIG. 6). The FPGAs receive focalization data from memories 728. The focalization data is utilized to manage the filters, delays and summing operations performed by the FPGAs in connection with beamforming. The beamformed RF or I/Q data is passed between the beamforming circuits 720 and ultimately to the digital processing board 626.

The digital front-end boards 610 also include transmit modules 722 that provide transmit drive signals to corresponding transducers of the ultrasound probe. The beamforming circuits 720 include memory that stores transmit waveforms. The transmit modules 722 receive transmit waveforms over line 724 from the beamforming circuits 720.

Figure 8:
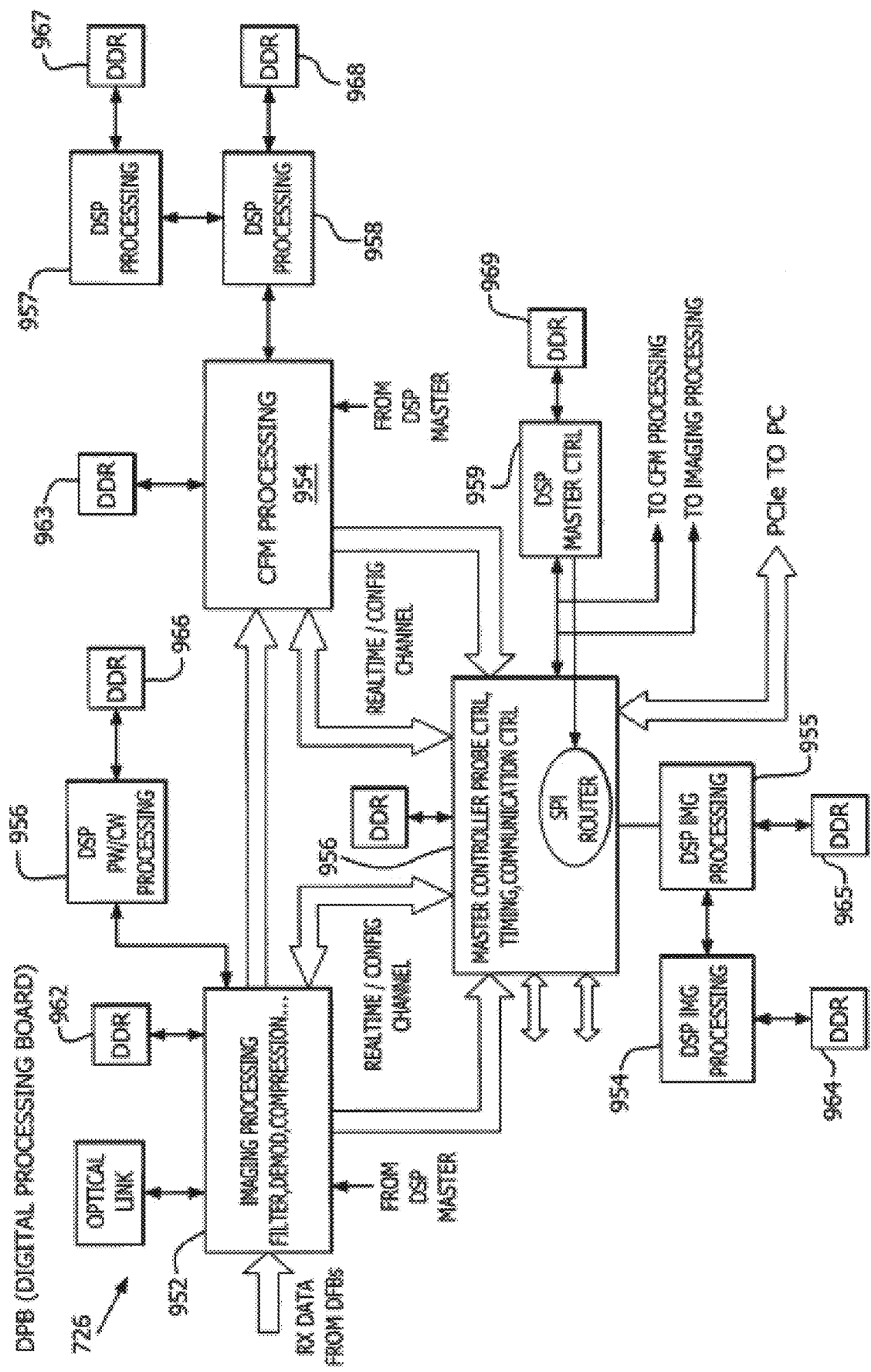
FIG. 8 illustrates a block diagram of the digital processing board.

FIG. 8 illustrates a block diagram of the digital processing board 626 implemented in accordance with embodiments herein. The digital processing board 626 includes various processors 852-859 to perform different operations under the control of program instructions saved within corresponding memories see 862-869. A master controller 950 manages operation of the digital processing board 626 and the processors 852-859. By way of example, one or more processors as the 852 may perform filtering, the modulation, compression and other operations, while another processor 853 performs color flow processing. The master controller provides probe control signals, timing control signals, communications control and the like. The master controller 850 provides real-time configuration information and synchronization signals in connection with each channel to the digital front-end board 610.

It should be clearly understood that the various arrangements and processes broadly described and illustrated with respect to the FIGURES, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

Aspects are described herein with reference to the Figures., which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

One or more of the operations described above in connection with the methods may be performed using one or more processors. The different devices in the systems described herein may represent one or more processors, and two or more of these devices may include at least one of the same processors. In one embodiment, the operations described herein may represent actions performed when one or more processors (e.g., of the devices described herein) execute program instructions stored in memory (for example, software stored on a tangible and non-transitory computer readable storage medium, such as a computer hard drive, ROM, RAM, or the like).

The processor(s) may execute a set of instructions that are stored in one or more storage elements, in order to process data. The storage elements may also store data or other information as desired or needed. The storage element may be in the form of an information source or a physical memory element within the controllers and the controller device. The set of instructions may include various commands that instruct the controllers and the controller device to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

The controller may include any processor-based or microprocessor-based system including systems using microcontrollers, reduced instruction set computers (RISC), application specific integrated circuitry (ASICs), field-programmable gate arrays (FPGAs), logic circuitry, and any other circuit or processor capable of executing the functions described herein. When processor-based, the controller executes program instructions stored in memory to perform the corresponding operations. Additionally or alternatively, the controllers and the controller device may represent circuitry that may be implemented as hardware. The above examples are exemplary only and are thus not intended to limit in any way the definition and/or meaning of the term "controller".

Optionally, aspects of the processes described herein may be performed over one or more networks one a network server. The network may support communications using any of a variety of commercially-available protocols, such as Transmission Control Protocol/Internet Protocol ("TCP/IP"), User Datagram Protocol ("UDP"), protocols operating in various layers of the Open System Interconnection ("OSI") model, File Transfer Protocol ("FTP"), Universal Plug and Play ("UpnP"), Network File System ("NFS"), Common Internet File System ("CIFS") and AppleTalk. The network can be, for example, a local area network, a wide-area network, a virtual private network, the Internet, an intranet, an extranet, a public switched telephone network, an infrared network, a wireless network, a satellite network and any combination thereof.

In embodiments utilizing a web server, the web server can run any of a variety of server or mid-tier applications, including Hypertext Transfer Protocol ("HTTP") servers, FTP servers, Common Gateway Interface ("CGI") servers, data servers, Java servers, Apache servers and business application servers. The server(s) also may be capable of executing programs or scripts in response to requests from user devices, such as by executing one or more web applications that may be implemented as one or more scripts or programs written in any programming language, such as Java®, C, C# or C++, or any scripting language, such as Ruby, PHP, Perl, Python or TCL, as well as combinations thereof. The server(s) may also include database servers, including without limitation those commercially available from Oracle®, Microsoft®, Sybase® and IBM® as well as open-source servers such as MySQL, Postgres, SQLite, MongoDB, and any other server capable of storing, retrieving and accessing structured or unstructured data. Database servers may include table-based servers, document-based servers, unstructured servers, relational servers, non-relational servers or combinations of these and/or other database serve The embodiments described herein may include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer or speaker). Such a system may also include one or more storage devices, such as disk drives, optical storage devices and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

Preferred embodiments of this disclosure are described herein, including the best mode known to the inventors for carrying out the invention. Variations of those preferred embodiments may become apparent to those of ordinary skill in the art upon reading the foregoing description. The inventors expect skilled artisans to employ such variations as appropriate and the inventors intend for embodiments of the present disclosure to be practiced otherwise than as specifically described herein. Accordingly, the scope of the present disclosure includes all modifications and equivalents of the subject matter recited in the claims appended hereto as permitted by applicable law.

Moreover, any combination of the above-described elements in all possible variations thereof is encompassed by the scope of the present disclosure unless otherwise indicated herein or otherwise clearly contradicted by context.

All references, including publications, patent applications and patents, cited herein are hereby incorporated by reference to the same extent as if each reference were individually and specifically indicated to be incorporated by reference and were set forth in its entirety herein.

The invention claimed is:

1. A method for generating ultrasound transmission waves comprising:
   a) providing an array of transducer elements, each transducer element being electroacoustic and connected to an electric excitation signal generator by a dedicated feeding channel;
   b) feeding at least a part of the transducer elements each with a respective pulsed electric excitation signal having a predetermined frequency, a predetermined amplitude, a predetermined length or duration and a predetermined phase or a predefined delay with respect to the pulsed electric excitation signals fed to the adjacent transducer elements, the pulsed electric excitation signals comprising a sequence of pulses;
   c) modulating each or at least part of the pulsed electric excitation signals by feeding to the transducer elements only a predetermined portion of the pulsed electric excitation signals,
   wherein operation c) is carried out by cutting the duration of the pulsed electric excitation signals according to at least one or more than one predetermined time intervals corresponding to a fraction of the pulsed electric excitation signals.

2. A method according to claim 1, wherein each of the respective pulsed electric excitation signals is cut off by putting the pulsed electric excitation signal to zero amplitude for a time interval corresponding to one time interval or for a series of time intervals each one of the time intervals of the series corresponding to a fraction of a pulse of the sequence of pulses forming the pulsed electric excitation signal.

3. A method according to claim 1, wherein the pulsed electric excitation signals driving each of said at least part of transducer elements of the array are formed by the sequence of pulses having a predetermined cycle and duration and the pulsed electric excitation signals have a predetermined total duration, while the duration of the time interval in which the pulse is cut off is applied to each pulse of the sequence of pulses.

4. A method according to claim 1, wherein the cutting the duration of the pulsed electric excitation signals in operation (c) comprises using a cut off of each pulse in a corresponding one of the pulsed electric excitation signals of the transducer elements that is different for at least part of the transducer elements and is set such that transducer elements at the outer edges of the array transmit a lesser percentage of a pulse in their corresponding pulsed electric excitation signals than the transducer elements located at the center of the array.

5. A method according to claim 1, wherein the cutting the duration of the pulsed electric excitation signals in operation (c) comprises using a cut off of the pulsed excitation signals or of the pulses of the pulsed excitation signals, the cut off beings carried out by shutting off or interrupting the feeding channel of the corresponding transducer element.

6. A method according to claim 1, further comprising:
   d) providing a probe having an array of transducer elements;
   e) carrying out operations a) to c) for a set of different periods of cut off for each one of the at least part of transducer elements and for each combination of cut off periods applied to said at least part of the transducer elements simulating by calculation a profile of the ultrasound wave theoretically generated by the array of transducer elements driven with said cut off periods or measuring the profile of the ultrasound wave generated by the array of transducer elements and saving the combination of cut off periods and the corresponding profile of the simulated or of the measured ultrasound wave;

f) generating a look up table describing the relation between profile of the generated ultrasound wave and a set of cut off periods for the at least part of transducer elements.

7. A method according to claim 6, wherein, once the look up table has been generated, said look up table is used for reading the values of the cut off periods corresponding to a desired acoustic wave profile comprising an apodization profile of the wave front of the transmitted ultrasound wave, and the cut off periods are applied to the pulsed electric excitation signals of the corresponding transducer elements for generating an ultrasound wave.

8. A method according to claim 6, further comprising selecting the look up table of the cut off periods corresponding to the probe;

generating pulsed electric excitation signals for at least part of the transducer elements;

modulating the pulsed electric excitation signals of the at least part of the transducer elements according to the cut off period taken from the look up table;

feeding the modulated pulsed electric excitation signals to the corresponding transducer elements.

9. A method according to claim 8, further comprising carrying out operations a) to f) to generate a look up table for each of a plurality of probes, and configuring an ultrasound system to automatically select a look up table corresponding to a selected one of the plurality of probes and to set the corresponding cut off periods of feeding lines corresponding to each or of part of the transducer elements in accordance with the selected look up table and comprising, when a certain probe is provided in the ultrasound system, upon choice of the profile of the generated ultrasound wave, using the data of the cut off periods from the selected look up table to control switches provided in the feeding lines of said transducer elements.

10. Ultrasound system comprising:

an ultrasound probe comprising an array of transducer elements that are electroacoustic;

an ultrasound transmit wave generating section configured to generate electric excitation signals of the transducer elements of the array;

said ultrasound transmit wave generating section comprising:

an ultrasound waveform generator which is connected by a separate feeding line with each one of the transducer elements or which can be connected with each one of the transducer elements alternatively from the other transducer elements;

a pulser unit for each of the transducer elements which is provided in the separate feeding line connected to a corresponding transducer element or which is provided in the feeding line which is alternatively connectable to each one of the transducer elements;

a control unit configured to control said pulser unit, which the control unit comprises means for modulating the pulsed signal generated by the pulser unit in such a way that only a predetermined portion of the pulsed signal or of pulses forming the pulsed electric signal is fed to the corresponding transducer element.

11. Ultrasound system according to claim 10, wherein the control unit is configured to cut the duration of said pulsed signal or of each pulse forming the pulsed electric signal according to a predetermined time period of cut off of the pulsed signal or of each pulse of the pulsed electric signal.

12. Ultrasound system according to claim 10, wherein said control unit is configured to directly operate on the pulser unit by activating and deactivating said pulser unit according to preestablished cut off periods of the pulsed signal or of the pulses of the pulsed electric signal of a corresponding transducer element.

13. Ultrasound system according to claim 10, wherein each feeding line is provided with a switch controllable by the control unit, said control unit being configured to commutate the switch to alternatively open or close the corresponding feeding line of a transducer element for predefined periods of conduction and of interruption of the feeding line.

14. Ultrasound system according to claim 10, further comprising:

a memory for saving a database or a look up table comprising a plurality of profiles of a wave front of a transmitted ultrasound wave and corresponding cut off periods to be applied to the feeding lines of each of the transducer elements of the array;

said database or said memory being readable by the control unit;

a wave front or apodization profile selector interface for selecting a wave front or apodization profile from the plurality of profiles and setting the selected wave front or apodization profile in the control unit;

said control unit being configured to automatically load the setting of the cut off periods related to the wave front or apodization profile for the respective feeding lines of the corresponding transducer elements and to apply the cut off periods in controlling opening and closing of said switches.

15. Ultrasound system according to claim 14, further comprising a probe selector for setting a type of ultrasound probe connected to the system among different types of probes compatible with said system, said selector being configured to automatically address and set the database or the look up table for the selected type of probe.

16. Ultrasound system according to claim 15, wherein the probe selector is an automatic selector configured to automatically receive or read information of the type of the connected probe and automatically address and set the database or the look up table for the selected type of probe.

* * * * *